US008634925B2

(12) United States Patent
Grandjean et al.

(10) Patent No.: US 8,634,925 B2
(45) Date of Patent: Jan. 21, 2014

(54) PORTABLE PROGRAMMER FOR PROVIDING PATIENT STATUS INFORMATION

(75) Inventors: Pierre A. Grandjean, Warsage (BE); Ilaria Vicini, Vimercate (IT); Barbro M. Kjellstrom, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1100 days.

(21) Appl. No.: 11/291,033

(22) Filed: Nov. 30, 2005

(65) Prior Publication Data
US 2007/0123786 A1 May 31, 2007

(51) Int. Cl.
*A61N 1/00* (2006.01)
(52) U.S. Cl.
USPC .......................................................... 607/59
(58) Field of Classification Search
USPC ............................ 607/59, 60, 30, 32; 600/300
See application file for complete search history.

(56) References Cited

U.S. PATENT DOCUMENTS

| 5,036,462 | A | * | 7/1991 | Kaufman et al. | 600/300 |
|---|---|---|---|---|---|
| 5,558,640 | A | * | 9/1996 | Pfeiler et al. | 604/67 |
| 5,722,999 | A | * | 3/1998 | Snell | 607/32 |
| 5,724,985 | A | | 3/1998 | Snell et al. | |
| 5,749,908 | A | * | 5/1998 | Snell | 607/30 |
| 5,759,199 | A | * | 6/1998 | Snell et al. | 607/60 |
| 5,810,735 | A | | 9/1998 | Halperin et al. | |
| 6,152,885 | A | | 11/2000 | Taepke | |
| 6,240,317 | B1 | | 5/2001 | Villaseca et al. | |
| 6,249,703 | B1 | * | 6/2001 | Stanton et al. | 607/30 |
| 6,331,160 | B1 | * | 12/2001 | Bardy | 600/300 |
| 6,363,282 | B1 | * | 3/2002 | Linberg | 607/60 |
| 6,453,201 | B1 | | 9/2002 | Daum et al. | |
| 6,497,655 | B1 | * | 12/2002 | Linberg et al. | 600/300 |
| 6,738,671 | B2 | * | 5/2004 | Christophersom et al. | 607/60 |
| 6,805,667 | B2 | | 10/2004 | Christopherson et al. | |
| 6,810,290 | B2 | * | 10/2004 | Lebel et al. | 607/60 |
| 2001/0047314 | A1 | * | 11/2001 | Linberg | 705/28 |
| 2002/0023654 | A1 | * | 2/2002 | Webb | 128/899 |
| 2002/0032470 | A1 | * | 3/2002 | Linberg | 607/60 |
| 2002/0040234 | A1 | * | 4/2002 | Linberg | 607/32 |
| 2002/0045804 | A1 | * | 4/2002 | Christopherson et al. | 600/300 |
| 2002/0072785 | A1 | * | 6/2002 | Nelson et al. | 607/60 |
| 2002/0193847 | A1 | * | 12/2002 | Daum et al. | 607/60 |
| 2003/0013945 | A1 | | 1/2003 | Graindorge et al. | |
| 2003/0041866 | A1 | * | 3/2003 | Linberg et al. | 128/899 |
| 2003/0171791 | A1 | * | 9/2003 | KenKnight et al. | 607/60 |
| 2004/0230247 | A1 | * | 11/2004 | Stein et al. | 607/32 |
| 2006/0136014 | A1 | * | 6/2006 | Simms, Jr. | 607/60 |
| 2006/0241712 | A1 | * | 10/2006 | Cates et al. | 607/30 |

OTHER PUBLICATIONS

International Search Report, PCT/US2006/060637, Dec. 4, 2007, 6 Pages.

* cited by examiner

*Primary Examiner* — Eric D. Bertram
*Assistant Examiner* — Roland Dinga

(57) ABSTRACT

A method and apparatus concerning the retrieval and storage of status information obtained from patients having implantable medical devices (IMDs). When patients are having episodes during which symptoms are experienced relating to their medical condition, the collection of the patient's status information can be helpful to the patient's physician for diagnostic purposes. Telemetered signals recorded by the IMD can be transmitted from the IMD to a programmer. Such programmer is portable and sized so as to be carried by the patient. As such, mechanisms added to such programmers for use in retrieving and storing patient status information can provide more convenience for patients.

12 Claims, 4 Drawing Sheets

PORTABLE PROGRAMMER FOR PROVIDING PATIENT STATUS INFORMATION

FIELD OF THE INVENTION

The disclosure relates generally to data collection and analysis, and more particularly, to a system and method for providing patient status information during symptomatic episodes.

BACKGROUND SECTION

Implantable medical devices (IMDs) are used to treat patients suffering from a variety of conditions. Examples of INDs involving cardiac devices are implantable pacemakers and implantable cardioverter-defibrillators (ICDs). Such electronic medical devices generally monitor the electrical activity of the heart and provide electrical stimulation to one or more of the heart chambers, when necessary. For example, pacemakers are designed to sense arrhythmias, i.e., disturbances in heart rhythm, and in turn, provide appropriate electrical stimulation pulses, at a controlled rate, to selected chambers of the heart in order to correct the arrhythmias and restore the proper heart rhythm. The types of arrhythmias that may be detected and corrected by such IMDs include bradycardias (unusually slow heart rates), which can result in symptoms such as fatigue, dizziness, and fainting, and certain tachycardias (unusually fast heart rates), which can result in sudden cardiac death (SCD).

Implantable cardioverter-defibrillators (ICDs) also detect arrhythmias and provide appropriate electrical stimulation pulses to selected chambers of the heart to correct the abnormal heart rate. In contrast to pacemakers, however, an ICD can also provide pulses that are much stronger and less frequent. This is because ICDs are generally designed to correct fibrillation, which is a rapid, unsynchronized quivering of one or more heart chambers, and severe tachycardias, during which the heartbeats are very fast but coordinated. To correct such arrhythmias, ICDs deliver low, moderate, or high-energy shocks to the heart.

Generally, IMDs are designed to provide a telemetry function. As such, the IMDs are configured to automatically transmit and measure data from remote sources by wire or other means. Typically, IMDs are equipped with an on-board, volatile memory in which telemetered signals can be stored for later retrieval and analysis. In addition, a growing class of cardiac medical devices, including implantable heart failure monitors, implantable event monitors, cardiovascular monitors, and therapy devices, can be used to provide similar stored device information. Typically, the telemetered signals can provide patient physiologic and cardiac information. This information is generally recorded on a per heartbeat, binned average basis, or derived basis, and involve, for example, atrial electrical activity, ventricular electrical activity, minute ventilation, patient activity score, cardiac output score, mixed venous oxygen score, cardiovascular pressure measures, time of day, and any interventions and the relative success of such interventions. Telemetered signals can also be stored in a broader class of monitors and therapeutic devices for other areas of medicine, including metabolism, endocrinology, hematology, neurology, muscular disorders, gastroenterology, urology, ophthalmology, otolaryngology, orthopedics, and similar medical subspecialties.

Generally, upon detecting arrhythmias and, when necessary, providing corresponding therapies to correct such arrhythmias, the IMDs store the telemetered signals over a set period of time (usually before, during, and after the occurrence of such arrhythmic event). Subsequently, current practice in the art involves the use of an external programming unit, i.e., a programmer, for non-invasive communication with IMDs via uplink and downlink communication channels associated with the programmer. In accordance with conventional medical device programming systems, a programming head can be used for facilitating two-way communication between IMDs and the programmer. In many known implanted IMD systems, the programming head is positioned on the patient's body over the IMD side such that one or more antennae within the head can send RF signals to, and receive RF signals from, an antenna disposed within the hermetic enclosure of the IMD or disposed within the connector block of the IMD in accordance with common practice in the art.

Upon storing the telemetered signals within the programmers, such data can be subsequently analyzed by the patient's physician for diagnostic purposes. Previously, the data stored within the programmers was downloaded during visits to the physician; however, recent technology has enabled the patient to download such data at home using, for example, a personal computer (PC) and a network to transmit the data to the physician.

For patients who require the use of IMDs, it is quite commonplace for the patient to have episodes during which symptoms are experienced, e.g. shortness of breath, palpitations, dizziness, extreme tiredness, etc. However, in some cases, these episodes occur when the IMDs are not sensing an arrhythmia, and as such, no telemetered signals are stored with respect to such episodes. However, the physiologic and cardiac data that can be collected during these episodes can be of extreme importance to the physician, as conclusions can be made (upon analyzing such data) as to the patient's general quality of life and the suitability of the IMD with respect to the patient. As such, during and/or following such episodes, the patient may be instructed to keep a written account (e.g., a written diary) of symptoms experienced. As such, this written account can be analyzed by the physician when analyzing telemetered signals that may have been stored by the IMD to date. However, this task of providing a written account of the symptoms experienced has generally been found by the patient to be cumbersome and often not done. In turn, this lack of information complicates analysis by the physician of the stored data and/or clinical treatment of the patient.

The embodiments of the invention are directed to overcoming, or at least reducing the effects of, one or more of the limitations set forth above.

SUMMARY OF THE INVENTION

Embodiments of the invention relate to the retrieval and storage of status information obtained from patients having implantable medical devices (IMDs). When patients are having episodes during which symptoms are experienced relating to their medical condition, the collection of the patient's status information can be helpful to the patient's physician for diagnostic purposes. Generally, telemetered signals recorded by the IMD can be transmitted from the IMD to a programmer. Such programmer is portable and sized so as to be carried by the patient. As such, mechanisms added to such programmers for use in retrieving and storing patient status information can provide more convenience for patients.

In some embodiments, a system for monitoring a patient's well being is provided. The system comprises a medical device implanted in a patient, where the medical device has circuitry for storing signals collected from the patient. The system also comprises a patient portable programmer having first circuitry for communicating with the medical device wherein the signals stored by the medical device can be telemetered to the programmer upon interrogation by the programmer. The programmer has second circuitry for receiving and storing status information from the patient regarding a condition being experienced by the patient.

In other embodiments, a programmer for capturing patient status information from a patient with an implantable medical device during episodes in which the patient experiences symptoms is provided. The programmer comprises a housing adapted to be carried by a patient. The programmer comprises first circuitry within the housing for communicating with an implantable medical device implanted within the patient, wherein signals stored by the implantable medical device can be telemetered to the first circuitry upon interrogation by the first circuitry. The programmer comprises second circuitry for receiving status information from the patient regarding a condition being experienced by the patient. The programmer comprises memory for storing the signals and the status information.

In further embodiments, a method of capturing status information from a patient with an implantable medical device during episodes in which the patient experiences symptoms is provided. The method comprises placing a programmer within a transmitting distance of a medical device implanted in a patient to trigger the medical device when the patient experiences a symptom. A further step includes transmitting signals collected by the medical device to the programmer. An additional step involves providing status information by the patient to the programmer. A further step involves storing the signals and the status information by the programmer in a memory of the programmer.

DETAILED DESCRIPTION OF THE PREFERRED EMBODIMENTS

Figure 1:
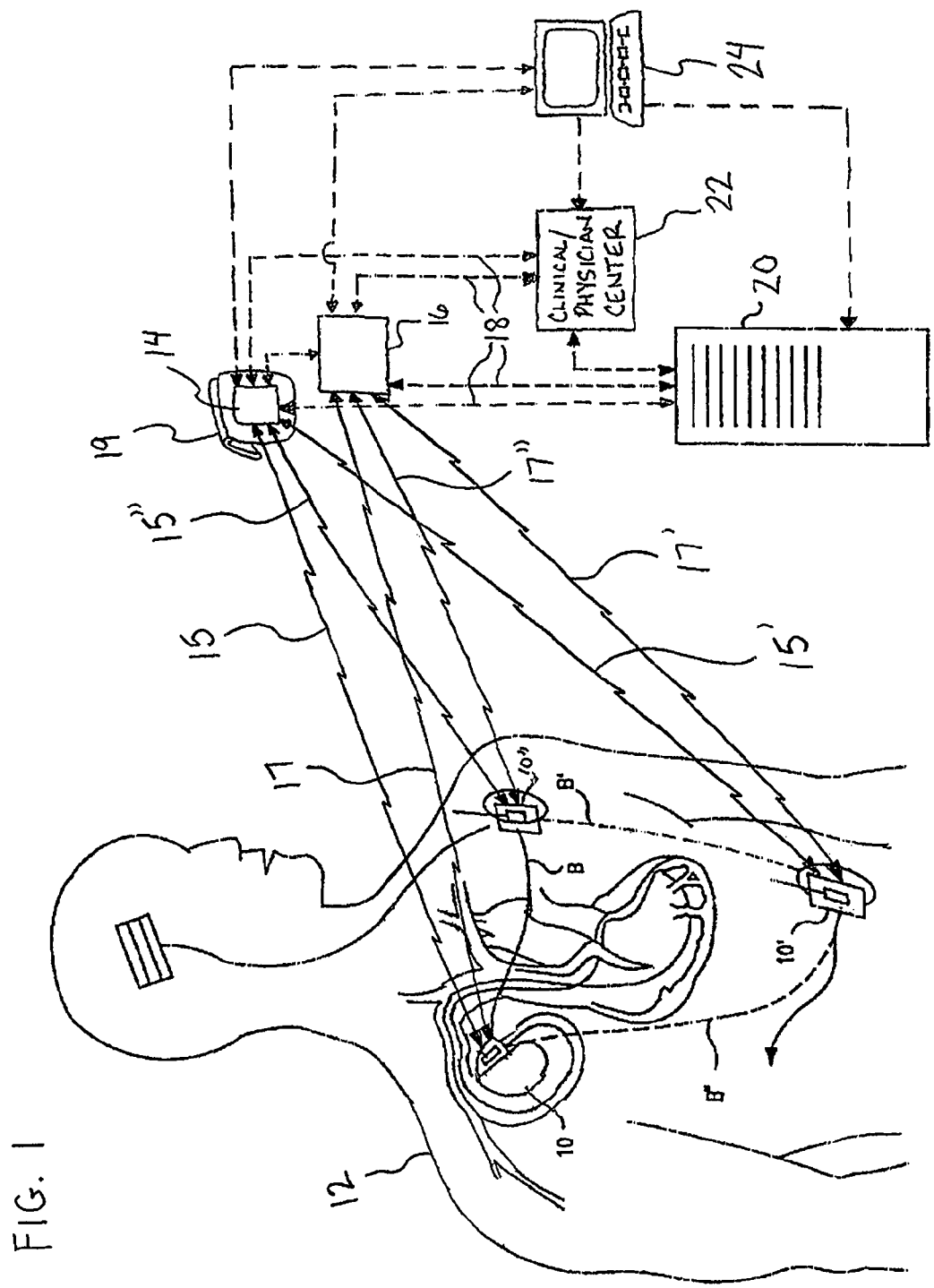
FIG. 1 is a simplified schematic diagram representation of a system in accordance with certain embodiments of the invention.

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

FIG. 1 is a simplified schematic diagram representation of a system in accordance with certain embodiments of the invention. As shown, one or more IMDs such as IMD 10, 10' and 10" can be implanted in a patient 12. In certain embodiments, one or more of the IMDs 10, 10' and 10" can have internal communications, B, B' and B". In certain embodiments, the IMDs include a cardiac device 10, drug delivery device 10', neurological drug device 10"; however, it is to be appreciated that fewer or additional IMDs may be used as needed to provide the necessary therapy, diagnosis and clinical care to the patient 12.

As discussed herein, telemetry communications can occur between the IMDs 10, 10', 10" and a programmer 14 and/or an information remote monitor (IRM) 16 when the programmer 14 and/or the IRM 16 is generally located within transmitting proximity of the IMDs 10, 10', and 10". As shown, the transmitting capability of the IMDs 10', 10', and 10" can be wide-ranging. In certain embodiments, as described herein, the programmer 14 and/or the IRM 16 tend to be positioned on the body of the patient 12 over the corresponding IMD to generally initiate such telemetry communications between the IMD and the programmer 14 and/or the IRM 16. Regarding telemetry communications 15 with the programmer 14 and/or telemetry communications 17 with the information remote monitor (IRM) 16, the IMD 10 is discussed herein; however, as illustrated in FIG. 1, it is to be appreciated that one or more of the other IMDs 10', 10" may also be used alternatively or in combination with the IMD 10 to respectively provide telemetry communications 15' and 15" with the programmer 14 and/or telemetry communications 17' and 17" with the IRM 16.

Embodiments of the invention generally involve periods of time when telemetered signals are collected by the IMD, periods of time when the telemetered signals are transmitted from the IMD 10, and subsequently, periods of time when the obtained signals are analyzed by a physician, physician's assistants, or other care providers. Typically, events triggering the IMD 10 can cause the telemetered signals to be collected and stored by the IMD 10. In certain embodiments involving cardiac applications, such collection is beat to beat for approximately eighteen minutes before and six minutes after the event. However, as described herein, the invention should not be limited to only cardiac applications. In certain embodiments involving cardiac applications, there can be three types of triggering events: (i) a bradycardia event, (ii) a tachycardia event, and (iii) a patient activated event. Generally, the bradycardia and tachycardia events automatically trigger the IMD 10, while the patient activated event requires a manual triggering of the IMD 10 by the patient 12. In certain embodiments, such manual triggering of the IMD 10 by the patient 12 involves a signal being sent to the IMD 10 through some action of the patient 12.

In certain embodiments, application of the programmer 14 within transmitting proximity of an antenna of the IMD 10 can facilitate such triggering. In certain embodiments, this triggering can further initiate a subsequent download of at least a portion of the telemetered signals from the IMD 10 to the programmer 14. In such embodiments, as should be appreciated, the IMD 10 would only subsequently download the signals if the programmer 14 is within transmitting proximity of the IMD 10. If not, the IMD 10 can be designed to download the data during a subsequent occasion when the programmer 14 is brought within transmitting proximity of the IMD 10, e.g., so as to trigger the IMD 10 again.

In using the programmer 14 for manual triggering of the IMD 10, in certain embodiments, a magnetized reed switch (not shown) within the IMD 10 closes in response to the placement of the programmer 14 over the location of the IMD 10. Generally, the programmer 14 includes a magnet (not visually shown), which facilitates the closure of the reed switch. Following the closure of the reed switch, the IMD 10 can communicate with the programmer 14 via RF signals. As such, if the programmer 14 is kept within transmitting proximity of the IMD 10, the stored telemetered signals can be downloaded from the IMD 10 into the programmer 14.

In certain embodiments, the IMD 10 is a Chronicle® implantable heart monitor, commercially available from Medtronic, Inc., located in Minneapolis, Minn. However, it is to be appreciated that the invention should not be limited to such a device. Generally, any form of implantable medical device suitable for storing telemetered signals or physiological data could be used, as known in the art. The Chronicle® is a hemodynamic monitor and can include circuitry for data storage, recovering and processing of pressure, electrogram, heart rate, core temperature, and activity data. The Chronicle® is generally used in patients with chronic Congestive Heart Failure (CHF), undergoing serial clinical management, and is typically used to complement existing CHF therapies and disease management regimens in order to provide precise therapy management, early intervention by remote monitoring of impending decompensation and to improve quality of life. The Chronicle® generally contains an operating system that may employ a microcomputer or a digital state machine for timing, sensing, data storage, recovery and processing of pressure, electrogram, heart rate and other related data, to thereby monitor the hemodynamic environment.

In certain embodiments, the programmer 14 is an external pressure reference monitor (EPR). However, it is to be appreciated that the invention should not be limited to such. Generally, any form of portable programmer, interrogator, recorder, monitor, sensor, or telemetered signals transceiver suitable for communicating with the IMD 10 could be used, as is known in the art. In certain embodiments, the programmer 14 is generally carried by a patient physically or through the use of a carrying implement 19, e.g., a clip, a belt, a wrist band, etc., so that the programmer 14 can be kept in close proximity to the patient 12, and in turn, the IMD 10. In certain embodiments, the carrying implement 19 can include a mechanism (e.g., a watch) that the programmer 14 is integrated with. An EPR is typically used to derive reference pressure data for use in combination with absolute pressure derived from an IMD. In addition, an EPR measures and records barometric pressure which is necessary for correlation to atmospheric pressure. Various embodiments of an EPR device are disclosed in U.S. Pat. No. 6,152,885 issued to Taepke, which patent is incorporated herein by reference in relevant part. Similarly, U.S. Pat. No. 5,810,735 to Halperin et al, which patent is incorporated herein by reference in relevant part, discloses external patient reference sensors of internal sensors.

As described above, in certain embodiments, communication 15 between the IMD 10 and the programmer 14 is generally initiated via direct antenna placement. In certain embodiments, the IMD 10 can employ an elongated antenna which projects outward from the housing of the IMD 10 as described in U.S. patent application Ser. No. 09/303,178, now published as U.S. Pat. No. 6,240,317, for "A Telemetry System for Implantable Medical Devices", filed Apr. 30, 1999 by Villaseca et al, which application is incorporated herein by reference in relevant part, or can employ a coil antenna located external the housing. Once downloaded, in certain embodiments, the telemetered signals and any other data stored within the programmer 14, can be sent, for example, from the patient's home, via an inter-network 18, such as the Internet, to a remote server 20 or remote clinical/physician center 22. In certain embodiments, the telemetered signals and other data are transmitted from the programmer 14 via transmission links, including but not limited to cellular phone links, LANS, RF links, regular phone lines, cable modems and the like.

As illustrated in FIG. 1, the programmer 14 can include software which is adaptable to enable communication with various types of IMDs, including but not limited to cardiac devices, neural implants, drug delivery systems and other medical devices. In certain embodiments, the programmer 14 is adapted for connection to a PC 24 for data transfer. In the alternate, the PC 24 may be used to control the programmer 14 to program the implanted device, thereby implementing the programmer 14 as a programming device. In certain embodiments, the programmer 14 can transfer the telemetered signals and data through the PC 24 to the server 20 or the remote clinical/physician center 22 via a modem and other wireless communications media. In certain embodiments, the programmer 14 can utilize an integral modem to dial a server and transfer data via FTP, PPP and TC/PIP protocols.

Figure 2:
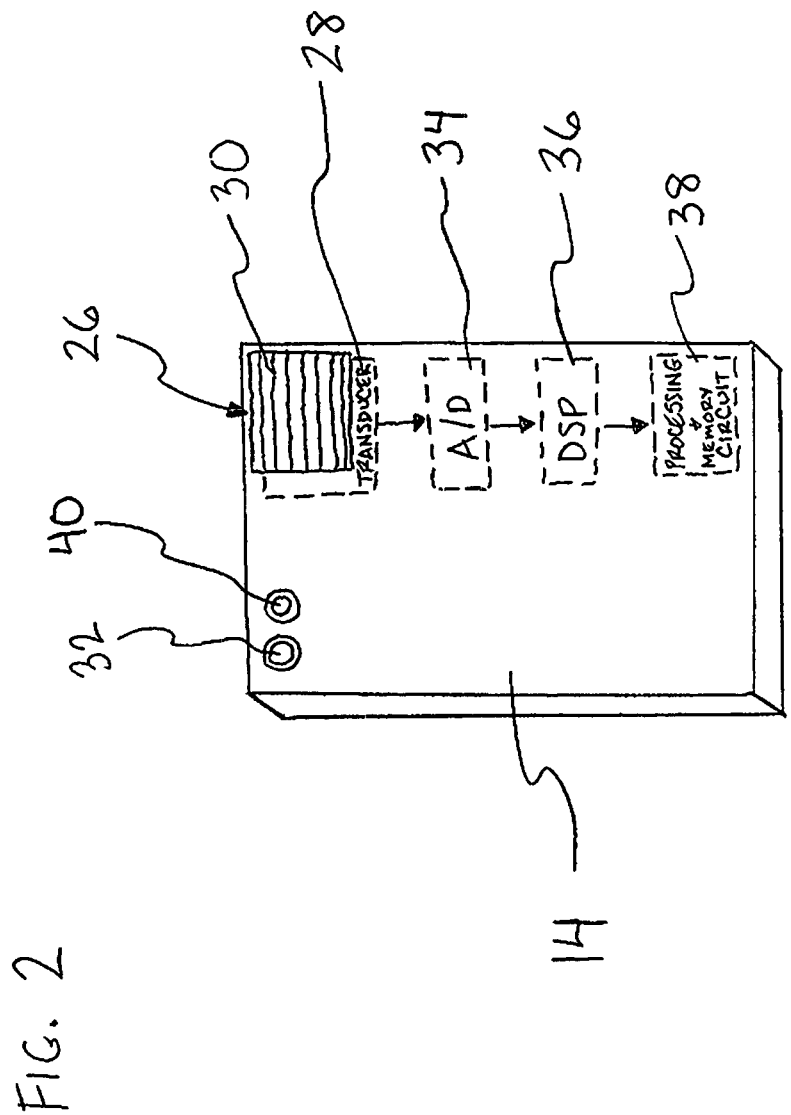
FIG. 2 is a plan view of a programmer in accordance with certain embodiments of the invention.

In certain embodiments, the programmer 14 is designed to include a microphone 26 and voice recording circuitry (shown in FIG. 2), where such circuitry is internal to the programmer 14. A transducer 28 (FIG. 2) can be provided, for example, under perforations 30 in the body of the microphone 26 in order to receive voice data from the patient 12. As shown in FIG. 2, when activated by the patient 12 (e.g., by depressing a "record" button 32 located on the programmer 14), the transducer 28 generally converts audio signals to analog electrical signals. In turn, an analog to digital (A/D) converter 34 preferably converts the analog electrical signals into digital data. Further, the digital data from the A/D converter 34 can be preprocessed by a digital signal processor (DSP) 36 before being passed to a processing and memory circuit 38 of the programmer 14. In other embodiments (not shown), the DSP 36 can be omitted and the digital data from the A/D converter 34 could be passed directly to the processing and memory circuit 38. Following such recording, the patient 12 can terminate the recording by, in certain embodiments, depressing a "stop" button 40 located on the programmer 14. In certain embodiments, the "record" and "stop" buttons 32, 40 respectively are recessed into the body of the programmer 14 to avoid accidental depression of the buttons when handling the programmer 14.

As mentioned above, the microphone 26 can be used to receive voice data from the patient. Similar techniques of recording voice data are suggested in U.S. Pat. No. 5,749,908 issued to Snell, which patent is incorporated herein by reference in relevant part. In certain embodiments, the patient 12 can use the microphone 26 and associated recording circuitry in the programmer 14 to store what is being felt during episodes in which the patient 12 experiences symptoms, e.g. shortness of breath, palpitations, dizziness, extreme tiredness, etc. Techniques of a patient recording symptoms are suggested in U.S. Pat. No. 6,331,160 issued to Bardy, which patent is incorporated herein by reference in relevant part.

As mentioned above, when the patient 12 has episodes in which the above-stated or other symptoms are experienced, quite often, the IMD 10 is not triggered. As such, in certain embodiments, the patient 12 is requested to trigger the IMD 10 upon experiencing these symptoms to store and transfer the telemetered signals associated therewith. By further designing the programmer 14 to include the microphone 26 and associated recording circuitry, the system enables the patient to describe their symptoms. As such, the system is convenient to the patient 12 as well as beneficial to the patient's physician. For example, such programmer design allows the patient 12 to record voice data at the same time or shortly after the time he is triggering the IMD 10 during a patient activated event, as the programmer 14 would generally be held over the position of the IMD 10 for triggering purposes and, as such, close to the patient's mouth for recording purposes. Additionally, such programmer design enables the technique of recording to be "ready made" for the patient 12, since the programmer 14, as described earlier, is designed to be portable and carried by the patient 12. Further, the programmer design allows the simultaneous storage of telemetered signals from the IMD 10 with digital data corresponding to voice recordings from the patient 12, so as to group such information together for subsequent analysis by the patient's physician. In certain embodiments, the signals and recordings are grouped through the use of a clock circuit (not shown) internally located within each of the IMD 10 and the programmer 14 to correspondingly mark the telemetered signals and digital data stored in the memory of the programmer 14.

Figure 3:
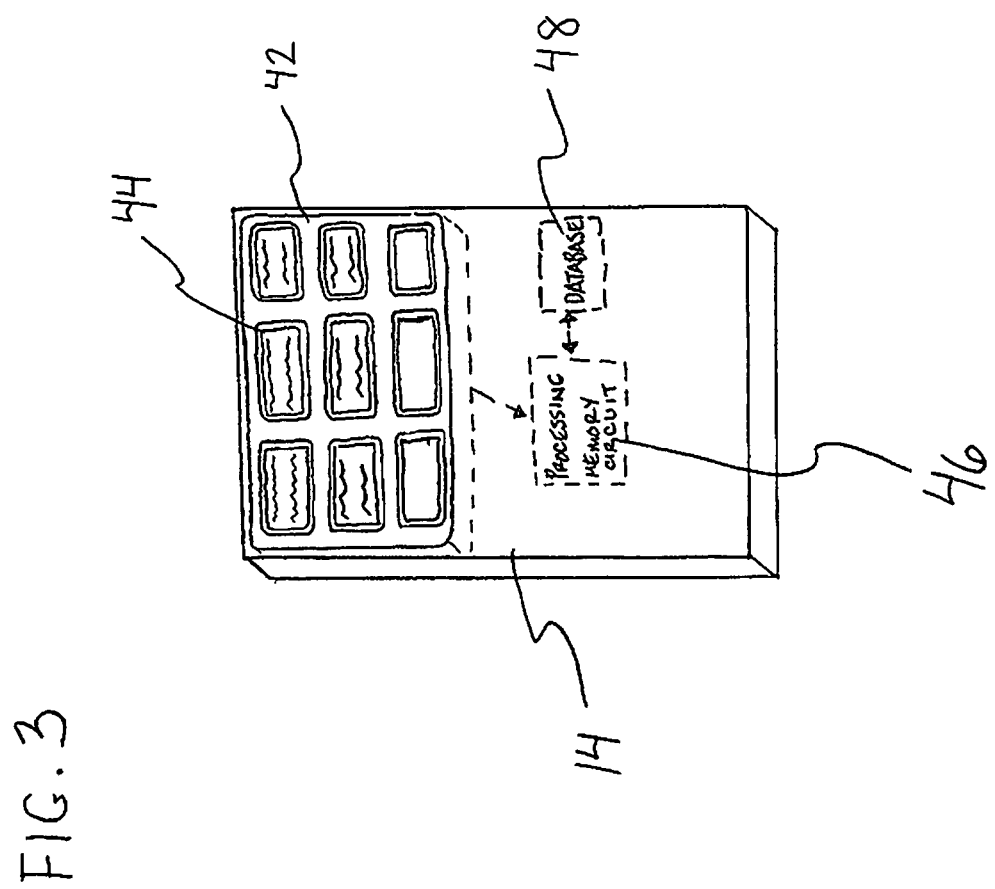
FIG. 3 is a plan view of another programmer in accordance with certain embodiments of the invention.

As shown in FIG. 3, in certain embodiments, the programmer 14 is designed to include a key pad 42 with a plurality of labeled keys 44 recessed into the body of the programmer 14. The keys 44 are recessed so as to avoid accidental depression of the keys 44 when handling the programmer 14. Similar to the function of the microphone 26 and recording circuitry discussed above, in certain embodiments, the patient 12 can use the labeled keys 44 on the programmer 14 and associated memory within the programmer 14 to store what is being felt during episodes in which the patient 12 experiences symptoms, e.g. shortness of breath, palpitations, dizziness, extreme tiredness, etc. In certain embodiments, each symptom that may potentially be experienced by the patient 12 is generally inscribed on a distinct label, with the labels being attached to separate keys 44. In certain embodiments, there may be one or more keys 44 that have no such inscription on their corresponding labels. As such, the physician can inscribe the one or more keys 44 with respect to symptoms that are frequently experienced by the patient, yet may not already be included on the keys 44 that were previously inscribed. In turn, the design of the programmer 14 can be altered so as to function accordingly with future depression by the patient 12 of such keys 44 inscribed via the physician.

In certain embodiments, when any one of the inscribed keys 44 is depressed by the patient 12, an electrical signal is sent from the depressed key 44 to a processing and memory circuit 46 within the programmer 14, where such processing and memory circuit 46 includes or is linked to a database 48. The database 48 is used to store a plurality of digital values, each value being associated with one of the symptoms labeled on the keys 44. In certain embodiments, upon receiving the electrical signal from the depressed key 44, the processing and memory circuit 46 is programmed to locate the corresponding digital value within the database 48, and store such value.

By further designing the programmer 14 to include the labeled keys 44 thereon and the processing and memory circuit 46 therein, the system enables the patient to indicate their symptoms. Thus, the system is convenient to the patient as well as beneficial to the patient's physician. For example, such programmer design allows the patient 12 to depress the key(s) 44 at the same time or shortly after the time the IMD 10 is triggered during a patient activated event. Locating and depressing the keys 44 on the programmer 14 which correspond to the symptoms being experienced would take a few seconds as the programmer 14 is generally held over the position of the IMD 10 for triggering purposes. Additionally, such programmer design enables the technique of depressing keys to be "ready made" for the patient 12, since the programmer 14, as described earlier, is designed to be portable and carried by the patient 12. Further, the programmer design allows the simultaneous storage of telemetered signals from the IMD 10 with digital values corresponding to the keys depressed by the patient 12, so as to group such information together for subsequent analysis by the patient's physician. In certain embodiments, the signals and digital values are grouped through the use of a clock circuit (not shown) internally located within the programmer 14 to correspondingly mark the telemetered signals and recordings stored in the memory of the programmer 14.

It is to be appreciated that, in certain embodiments, the programmer 14 may incorporate both the microphone 26 and voice recording circuitry as shown in FIG. 2 and the key pad 42 with a plurality of pre-labeled keys 44 as shown in FIG. 3. In using the programmer 14 with additional functions as described with respect to FIGS. 2 and/or 3, the patient can more readily and conveniently record what is being experienced during such symptomatic episodes. As such, by using one or more of these functions of the programmer 14, the patient would no longer need to keep a written account (e.g., a written diary) of symptoms experienced over time. In turn, this stored patient status information can be used by the physician when analyzing telemetered signals stored by the IMD to date to aid in treating the patient 12.

As shown in FIG. 1, in certain embodiments, the programmer 14 can be adapted to communicate with an information remote monitor (IRM) 16 as mentioned with respect to FIG. 1. In use, the IRM 16 can be positioned a certain transmitting distance from the programmer 14 to enable the transmission of the telemetered signals and patient status information (e.g., digital data corresponding to voice recordings or keys depressed by the patient 12 on the programmer 14) from the programmer 14. Additionally, the IRM 16 can also be so positioned from the IMD 10 to enable telemetry communication 17 of any other telemetered signals held by the IMD 10 which may not be stored by the programmer 14. In certain embodiments, wireless communication between the IRM 16 and the programmer 14 and/or the IMD 10 may be implemented using, for example, various types of RF signals blue tooth or equivalent, for downloading the signals from the IMD 10 and/or the programmer 16 to the IRM 14. Following transfer of the data from the programmer 14 and/or IMD 10, the IRM 16 can be used from a patient's home to subsequently transmit the data to the remote server 20 and/or the remote clinical/physician center 22 to enable remote and chronic patient monitoring and management.

In certain embodiments, the data is sent, for example, from the patient's home via the inter-network 18, such as the Internet, to the remote server 20 or remote clinical/physician center 22. In certain embodiments, the data is transmitted from the IRM 16 via transmission links, including but not limited to cellular phone links, LANS, RF links, regular phone lines, cable modems and the like.

As illustrated in FIG. 1, the IRM 16 can include software so as to enable communication with various types of IMDs, including but not limited to cardiac devices, neural implants, drug delivery systems and other medical devices. In certain embodiments, the IRM 16 is adapted for connection to the PC 24 for data transfer. In the alternate, the PC 24 may be used to control the IRM 16 to program the implanted device, thereby implementing the IRM 16 as a programming device. In certain embodiments, the IRM 16 can transfer the data through the PC 24 to the server 20 or the remote clinical/physician center 22 via a modem and other wireless communications media. In certain embodiments, the IRM 16 can utilize an integral modem to dial a server and transfer data via FTP, PPP and TC/PIP protocols.

Figure 4:
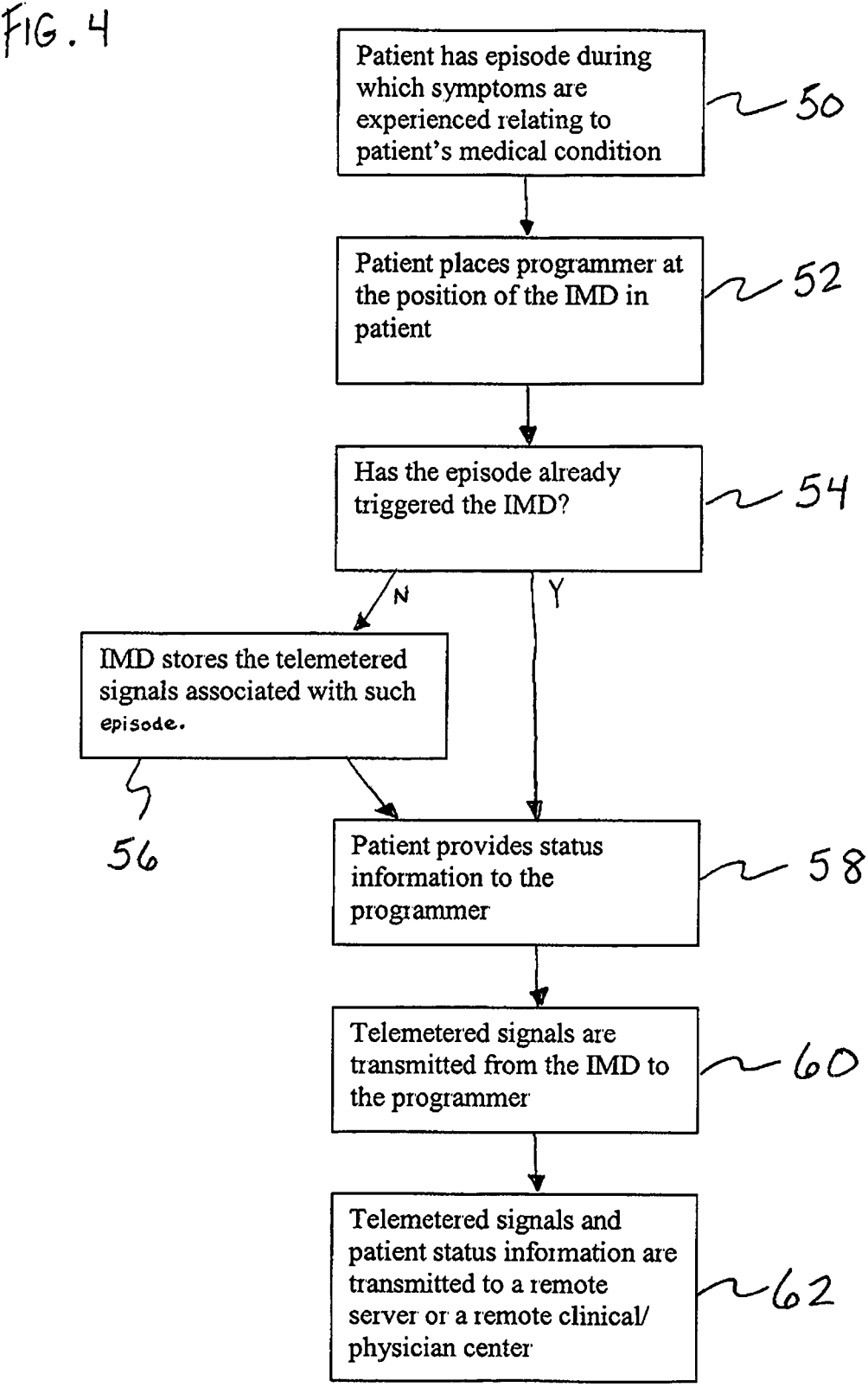
FIG. 4 is a flowchart showing the steps taken by a patient during a patient activated event in accordance with certain embodiments of the invention.

FIG. 4 is a flowchart showing the steps taken by a patient during a patient activated event in accordance with certain embodiments of the invention. An initial step 50 involves the patient 12 with IMD 10 (FIG. 1) having an episode in which he/she experiences symptoms, e.g. shortness of breath, palpitations, dizziness, extreme tiredness, etc. Upon feeling such symptoms, the patient 12 places the programmer 14 above the position of the IMD 10 in the patient 12 to trigger the IMD 10 in step 52. As mentioned herein, such symptoms experienced by the patient 12 may often not result in a triggering of the device; however, there are cases in which the IMD 10 is triggered by such symptoms. Such question regarding the state of triggering of the IMD 10 is shown in step 54. If the IMD 10 is triggered by placing the programmer 14 at the position of the IMD 10, step 56 involves the IMD 10 storing the telemetered signals associated with such event for a preprogrammed period of time. If the IMD 10 had already been triggered by the symptoms, step 56 is skipped, as shown. Step 58 involves the patient 12 providing status information as to the symptoms being experienced. In certain embodiments, steps 56 and 58 can take place at the same time.

With further reference to FIG. 4, step 60 involves transmitting the collected telemetered signals from the IMD 10 to the programmer 14. As described above, step 60 and subsequent steps can occur during a subsequent triggering of the IMD 10 if the programmer 14 is not kept within transmitting proximity of the IMD 10 during the prior triggering. Step 62 involves transmitting the telemetered signals and patient status information to the remote server 18 and/or the remote clinical/physician center 20 for remote and chronic patient monitoring and management. If IRM 16 is provided in the system, a further step can be involved between steps 60 and 62 involving transmitting the telemetered signals from the IMD and/or the programmer 14.

It will be appreciated the embodiments of the present invention can take many forms. The true essence and spirit of these embodiments of the invention are defined in the appended claims, and it is not intended the embodiment of the invention presented herein should limit the scope thereof.

What is claimed is:

1. A system for monitoring a patient's well being, the system comprising:
    a medical device adapted to be implanted in a patient, the device having circuitry configured to store signals collected from the patient and circuitry configured to trigger the medical device for collection of the signals from the patient in response to manual action of the patient; and
    a patient portable programmer, the programmer having first circuitry configured to communicate with the medical device wherein the signals stored by the medical device can be telemetered to the programmer upon interrogation by the programmer, the programmer having second circuitry configured to receive and store status information from the patient apart from the signals telemetered from the medical device, the status information stemming from manual input by the patient to the programmer via a keypad with a plurality of keys, wherein each of the keys is associated with a different one of a plurality of symptoms that the patient may experience, the status information indicating which one or more of the symptoms is being experienced by the patient, the symptoms comprising one or more of shortness of breath, palpitations, dizziness, and extreme tiredness.

2. The system of claim 1, wherein the medical device comprises an implantable heart monitor.

3. The system of claim 1, further comprising one or more medical machines implanted in the patient, wherein the medical device is in communication with at least one of the one or more medical machines.

4. The system of claim 3, wherein the signals comprise physiological information from one or more of the medical device and the medical machines.

5. The system of claim 1, wherein the programmer comprises an external pressure reference monitor.

6. The system of claim 1, wherein the programmer is operatively coupled to an implement adapted to be worn by the patient.

7. The system of claim 6, wherein the implement includes a mechanism that the programmer is integrated with.

8. The system of claim 1, wherein the second circuitry of the programmer is adapted for receiving and storing patient voice data.

9. The system of claim 8, wherein the second circuitry of the programmer comprises a microphone and voice recording circuitry.

10. The system of claim 1, wherein the second circuitry of the programmer is adapted for receiving and storing data input by the patient.

11. The system of claim 1, wherein the positioning of the programmer is within transmitting proximity of the medical device, wherein the status information provided from the patient to the programmer is simultaneous with the manual triggering of the medical device.

12. The system of claim 1, wherein the circuitry for triggering of the medical device comprises a reed switch, and wherein the positioning of the programmer for manual triggering comprises placing at least a portion of the programmer above the medical device.

* * * * *